United States Patent [19]
Valette et al.

[11] Patent Number: 5,073,024
[45] Date of Patent: Dec. 17, 1991

[54] INTEGRATED OPTICAL DEVICE FOR MEASURING THE REFRACTIVE INDEX OF A FLUID

[75] Inventors: Serge Valette, Grenoble; Stéphane Renard, Champ sur Drac, both of France

[73] Assignee: Commissariat a l'Energie Atomique, Paris, France

[21] Appl. No.: 426,425

[22] Filed: Oct. 24, 1989

[30] Foreign Application Priority Data

Nov. 4, 1988 [FR] France .................. 88 14433

[51] Int. Cl.$^5$ .................. G01B 9/02
[52] U.S. Cl. .................. 356/345; 356/361
[58] Field of Search .................. 356/128, 345, 361

[56] References Cited

U.S. PATENT DOCUMENTS 4,865,453 9/1989 Gidon et al. .................. 356/358
4,950,074 8/1990 Fabricius et al. .................. 356/361 X

FOREIGN PATENT DOCUMENTS 0286528 10/1988 European Pat. Off. .

OTHER PUBLICATIONS

The Transactions of the Institute of the I.E.I.C.E., vol. E71, No. 4, 4/1988, M. Doi et al.
Sov. J. Quant, Electron, vol. 6, No. 2, 2/1976, E. Zolotov Electronics Letters, vol. 21, No. 6, 3/1985, P. O. Andersson et al.

Primary Examiner—Davis L. Willis
Assistant Examiner—Matthew W. Koren
Attorney, Agent, or Firm—Cesari and McKenna

[57] ABSTRACT

An integrated optical device for measuring the refractive index of a fluid comprises a light guide formed on a substrate and having a guiding layer for carrying light beams, inserted between a lower layer and an upper layer having refractive indices below that of the guiding layer. The device includes an interaction measurement zone of the light guide for coming into contact with the fluid, the upper layer at the measurement zone having a thickness less than the penetration distance of the evanescent wave of the guided light beam. Outside the interaction zone, that upper layer has a thinckness greater than the penetration distance of the same evanescent beam. The device also has an interferometric optical system at least partly formed in the light guide and having a reference optical circuit and a measurement optical circuit including the measurement zone, for measuring the phase shift introduced by an effective index change of the guided mode due to the fluid.

23 Claims, 5 Drawing Sheets

INTEGRATED OPTICAL DEVICE FOR MEASURING THE REFRACTIVE INDEX OF A FLUID

The invention relates to a device of the interferometric type for measuring the refractive indices of liquids or gases, intended to operate in integrated optical structures.

The invention can be used in all fields where it is wished to know the refractive index of a fluid. In particular, the measurement of the refractive index of a gas can make it possible to determine the nature of said gas and its concentration. This is of particular interest in the case of a dangerous or toxic gas mixed with other gases.

In the same way, the measurement of the refractive index of a liquid can make it possible to determine the nature and density of said liquid which makes it possible to make use of parameters such as the pH, the dilution or the concentration, the pH and the dilution in particular making it possible to determine the charge state of a battery.

One of the best ways of measuring a refractive index of a fluid is obviously the use of an optical method. At present, the measurements of a refractive index of a fluid are based on modifications to the reflection conditions at the interface between the fluid having an unknown index and a medium having a known index.

However, this method suffers from a certain number of disadvantages. In particular, the reflection coefficient between two media of different refractive index varies relatively little with the refractive index of one of the two media, in particular that to be measured, the second medium being assumed fixed. Therefore this method is not very accurate, except in two particular use cases referred to hereinafter.

Figure 1:
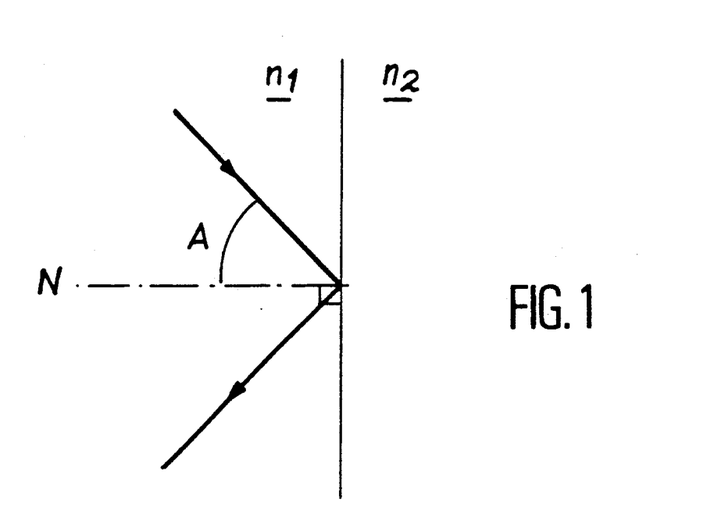
FIG. 1, already described, diagrammatically the reflection of a light beam at the interface of two media.

The two media are $n_1$ and $n_2$ as shown in the attached FIG. 1, with $n_2$ being the refractive index to be measured and $n_1$ the refractive index assumed to be fixed. In FIG. 1, A represents the angle of incidence of light, with respect to the normal N at the interface of the two media $n_1$-$n_2$.

When the angle of incidence A is high, particularly when the light is polarized in the plane of incidence, due to the existence of the Brewster angle for which the reflection coefficient Rp corresponding to the reflection coefficient in accordance with a polarization of the light parallel to the plane of incidence is zero, the aforementioned method can be used.

This method can also be used in the vicinity of the total reflection if the latter takes place, i.e. if $n_1$ exceeds $n_2$ and if A exceeds the total refraction angle. This limit angle $A_l$ is equal to $\text{Arsin}(n_2/n_1)$.

Thus, in the second case the method can only function if $n_1 > n_2$ and if $n_2$ varies relatively little, in view of the fact that the variations of the reflection coefficient are only significant in the vicinity of the limit angle. Thus, in the vicinity of the limit angle, the variation of even a small refractive index induces a considerable variation in the reflection coefficient.

Therefore this method is very limited and does not make it possible to measure any random type of refractive index on any variation range and under any lighting condition.

The invention consequently relates to a device for measuring the refractive index of a fluid, which is usable in a much more general manner, under any lighting condition and with any variation range of said index.

Within the scope of the invention, measurement of the refractive index of a fluid also covers the measurement of the relative and the absolute refractive index thereof.

The relative refractive index of a fluid corresponds to the variation of the index of said fluid with respect to a reference refractive index. This reference index can be the index of said fluid in a known state, or the index of a random fluid in a known state.

The measurement of the absolute index of the fluid is obtained either from the relative refractive index and the reference index, or directly (only in the case of an interference half-fringe).

The principle of the device according to the invention is based on phase variations supplied by the change to the refractive index of an unknown medium with respect to a known medium, said phase variations being measured by an interferometric system. This measurement method can be carried out either with a standard optical circuit, or with an integrated optical circuit.

Due to compactness, the dimensions of the circuit, compatibility with the optical fibers and finally the low cost, integrated optics is far and away the most promising construction technology for a device for measuring the refractive index of a fluid. The invention also relates to an interferometric integrated optical device making it possible to measure the refractive index of a medium in which the measuring device can be immersed. Thus, the latter can only be used for gases or liquids.

More specifically, the present invention relates to an integrated optical device for measuring the refractive index of a fluid comprising (a) a light guide corresponding to an effective index $n_1$ of the guided mode, formed on a substrate and having a guiding layer for carrying light beams, inserted between a lower layer and an upper layer having refractive indices below that of the guiding layer, (b) an interaction measuring zone of the light guide to be in contact with the fluid, the upper layer level with the measuring zone having a thickness smaller than the penetration distance of the evanescent wave of the guided light beam and outside said interaction zone a thickness greater than the penetration distance of said same evanescent wave, and (c) an interferometric optical system, at least partly formed in the light guide and having a reference optical circuit and a measuring optical circuit including the measuring zone, in order to measure the phase shift introduced by a change to the effective index $n_2$ of the guided mode due to the fluid.

This device makes use of the fact that, in integrated optics, the effective index of a guided mode is dependent on all the parameters of the structure of the guide and in particular the thickness and refractive indexes of the different layers constituting said guide. Moreover, the modification of one of these parameters and in particular the refractive index of one of the layers, modifies the effective index of the considered guided mode and consequently locally introduces a phase modification of the light which can be detected by interferometry.

It is preferable that the measuring or interaction zone of the guide with the fluid whose refractive index it is wished to know, have a structure such that the guided light continues to be guided. In addition, it must be protected from any influence of media other than the unknown media on the interaction zone.

In the device according to the invention, the use of an upper layer level with the measurement interaction zone and having a thickness less than the penetration distance of the evanescent wave associated with the guided mode means that the latter "sees" the medium of the index to be measured. To the extent that said index to be measured remains below the effective index of the guided light in said measurement interaction zone, the light remains guided throughout the structure. This condition constitutes an advantageous operating mode for the device. Conversely, in the zones where the upper layer thickness is greater than the penetration distance of said same guided mode, the latter does not see the external medium of the index to be measured.

When the external medium of unknown index is corrosive, which is the case in battery electrolytes, for which the device according to the invention makes it possible to measure the charge state, it is necessary for the interaction measurement zone to have as the upper layer a material which is not attacked by the external medium, whose refractive index it is wished to know. In addition, if the material of the upper layer may be attacked, use is made of a supplementary protective layer placed on the upper layer of the guide and whose thickness, at the measurement zone, is such that the sum of the thicknesses of the upper layer and the additional protective layer, at the interaction zone, is less than the penetration distance of the evanescent wave of the guided wave, when the protective layer has a refractive index below the effective index of the guided mode.

When the refractive index of the protective layer exceeds or is equal to the effective index of the guided mode, the latter still sees the external medium in the interaction zone. However, as will be described in more detail later, it is advantageous in the latter case to have a protective layer of thickness h'', such that the light guide remains of a monomode nature.

Only the interaction zone must be protected from the external medium to be measured, when a protective system equipped with seals is provided for insulating the measurement zone from the remainder of the circuit and in particular from the measuring and reference circuits.

The device according to the invention can be produced in silicon technology or III-V technology (GaAs or InP), which are very appropriate for integrated electronics.

Preferably, a silicon technology is used. In this case, the guiding layer is made from silicon nitride or a silica doped with phosphorus or titanium and the upper and lower layers of the optical guide are made e.g. from pure silica or glass. Silica and glass have refractive indices varying between 1.45 and 1.9 for a wavelength of 800 nm, while phosphorus-doped silica has an index between 1.45 and 1.5, as a function of the phosphorus percentage introduced and for a wavelength of 800 nm. Silicon nitride has a high refractive index close to 2 for a wavelength of 800 nm.

In the case of an acid, such as sulphuric acid, the protective material resistant to said acid is in particular alumina, which has a refractive index of approximately 1.61 (for 800 nm), or silicon nitride. In the latter case, the upper layer of the light guide can have a zero thickness in the interaction measurement zone.

According to a first embodiment, the interferometric device making it possible to measure the phase shift introduced by the medium having the refractive index to be measured comprises:
a light source emitting a main incident light beam,
means for collimating the main beam,
first splitting means for splitting the collimated main beam into a measurement beam and a a main reference beam and for directing the measurement beam onto the measurement zone,
a first mirror for reflecting the measurement beam from the measurement zone onto the first splitting means,
phase shifting means for introducing at least one constant phase shift on part of the main reference beam, in order to form at least two secondary phase shifted reference beams,
a second mirror for reflecting the two secondary reference beams onto the first splitting means, in order to make them respectively interfere with the measurement beam and thus form at least two first separate interference light signals, said first interference signals representing the refractive index of the fluid in contact with the measurement zone,
second splitting means for splitting the first two interference signals and
at least two detectors for in each case detecting a first interference signal,
the collimation means, the first and second splitting means and the phase shifting means being respectively formed by an appropriate local modification of the effective index of the light beam, and the mirrors being formed by a local and at least partial etching of the light guide.

According to a second embodiment, the interferometric device making it possible to measure the phase shift introduced by the medium with the refractive index to be measured comprises:
a light source emitting a main incident light beam,
means for collimating the main beam,
first splitting means for splitting the main collimated beam into a measurement beam and a main reference beam and for directing the measurement beam onto the measurement zone,
a first mirror for reflecting the measurement beam from the measurement zone onto second splitting means,
phase shifting means for introducing at least one constant phase shift onto part of the main reference beam, in order to form at least two secondary phase shifted reference beams,
a second mirror for reflecting the two secondary reference beams onto the second splitting means, so as to respectively make them interfere with the measurement beam and thus form at least two first separate interference light signals, said first interference signals representing the refractive index of the fluid in contact with the measurement zone,
third splitting means for splitting the first two interference signals and
at least two detectors for in each case detecting a first interference signal,
the collimating means, the first, second and third splitting means and the phase shifting means being respectively formed by an appropriate local modification of the effective index of the light guide, and the mirrors being formed by a local and at least partial etching of the light guide.

When the phase shifting means of the second embodiment are located between the first splitting means and the second mirror, the latter effectively receives the two secondary reference beams and transmits directly said two secondary reference beams onto the second splitting means. When these phase shifting means are located between the second mirror and the second splitting means, said second mirror in reality receives the main reference beam, which it supplies directly to the phase shifting means. This main beam is then split into two secondary reference beams by the phase shifting means, which then directly transmit these two secondary reference beams to the second splitting means.

In order to recover all the light energy passing out of the first splitting means and therefore all the interference signals formed on these first means for the first embodiment of the interferometric device and formed on the second splitting means for the second embodiment of the interferometric device, supplementary splitting means associated with second detectors are provided for splitting and detecting second interference signals formed simultaneously with the first interference signals.

The use of at least two interference systems makes it possible to obtain the phase shift introduced by the index variations of the unknown fluid with maximum sensitivity and avoid any ambiguity with regards to the value of the index to be measured when the latter increases and then decreases again leading to a sign change on the phase shift, which is undetectable if said phase shift is close to $k\pi$. The existence of a phase shift in the vicinity of $k\pi$ cannot exist on the two interference systems simultaneously, because they are phase shifted by a value different from $\pi$. In particular, the phase shift introduced is preferably equal to $\pi/2$.

In general, the light supplied by the source is carried by an optical input fiber, in order to improve the coupling between the light source and the rest of the integrated optical device. This input fiber is generally of a monomode nature and, in certain cases, maintains polarization. This is necessary in the case of an optical guide formed on a silicon substrate of structure $SiO_2/Si_3N_4/SiO_2$.

With a waveguide of a different structure and in particular of a $SiO_2$-doped $Si/SiO_2/SiO_2$ type, the input fiber can be of a multimode nature. Under these conditions, a collimating optics at the output of the multimode fiber must be provided for ensuring the injection of light into the waveguide.

The detectors of the interference signals, like the source, are located outside the light guide. In addition, output fibers can be provided between the optical guide and the detectors, whereby said fibers can be of a multimode or monomode nature.

The invention is described in greater detail hereinafter relative to non-limitative embodiments and the attached figures, wherein show.

Figure 2:
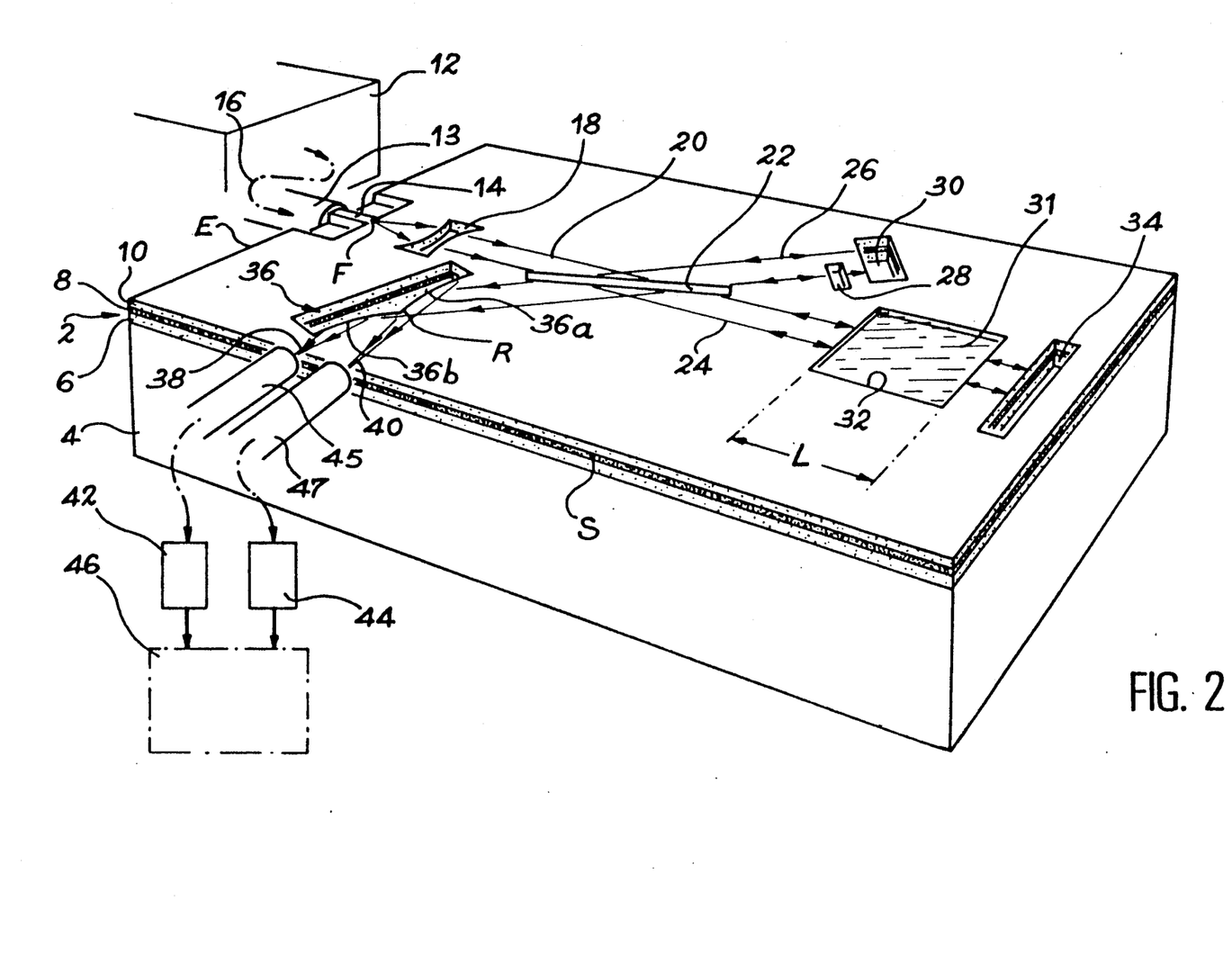
FIG. 2 Diagrammatically and in perspective, a first embodiment of the optical device according to the invention.

As shown in FIG. 2, the integrated device according to the invention comprises a light guide 2 advantageously on a silicon monocrystalline substrate 4. The optical guide 2 is constituted by three superimposed layers, respectively 6, 8 and 10 starting from the substrate 4, layer 8 constituting the guide layer for the optical guide. Layer 8 has a refractive index higher than that of layers 6 and 10. In particular, layers 6 and 10 are made from pure silica and layer 8 from silicon nitride.

The thickness of the guide layer 8 is between 10 and 250 nm in an approximate manner in order that guide 2 is of a monomode nature. The silica thicknesses of layers 6 and 10 are dependent on that of the nitride layer. They are between 1 and 5 $\mu$m in order to ensure a good light insulation respectively of the absorbent substrate 4 for layer 6 and the external medium for layer 10.

The silica layer 6 can be obtained by thermal oxidation of the substrate followed by chemical vapor deposition, which makes it possible to obtain better optical qualities than if said layer 6 was obtained by direct CVD on the substrate. The nitride layer 8 is obtained by LPCVD or PECVD. The upper layer 10 of guide 2 is obtained by PECVD.

The major part of the optical components of the device according to the invention is defined in said light guide.

External of guide 2, the optical device of FIG. 2 has a light source 12, such as a laser. A preferably monomode input fiber 13 collects the light from the source and ensures its injection into the guide layer 8 via a microguide 14.

The light beam 16 carried by fiber 13 and then microguide 14 is received by a integrated collimating lens 18, which makes it possible to transform the light from microguide 14, which can be likened to a light point, into a parallel light beam 20. For this purpose, the end of the microguide 14 facing lens 18 must be in the focus F of the latter.

The collimated light beam 20 then acts on a beam splitting plate 22 here constituted by a groove etched in the upper layer 10 of the optical guide. Plate 22 makes it possible to form a measurement beam 24 and a reference beam 26, respectively obtained by transmission and reflection of the incident beam on plate 22.

A phase shifter 28 placed on the reference beam 16 makes it possible to split the latter into two reference beams phase shifted by $\pi/2$ or $(2k+1)\pi/2$.

An interaction zone 32 to be in contact with the fluid 31, whose refractive index is to be measured, is formed in guide 2 and is traversed by the measurement beam 24.

A plane mirror 30 makes it possible to reflect the two phase shifted reference beams onto the beam splitting plate 22. In the same way, a plane mirror 34 makes it possible to reflect the measurement beam 24, via interaction zone 32, onto the beam splitting plate 22, in such a way that the measurement beam 24 and the two reference beams interfere and form two interference light signals representing the refractive index of the fluid 31 in contact with the interaction zone 32.

In the represented embodiment, the mirrors 30 and 34 are positioned perpendicular to the reference beam 26 and measurement beam 24. The beams reflected by these two mirrors consequently coincide with the corresponding incident beams.

The two interference systems formed on the splitting plate 22 are phase shifted by $\pi/2$ or $(2k+1)\pi/2$. They are received by a beam splitting or separating mirror 36 having an input phase formed by two parabolic parts 36a, 36b, whose tangents at the meeting point R form between them an angle between 120° and 180°, giving rise to two separate interference signals 38, 40 respectively detected by two photodetectors 42, 44, which can be attached to the light guide 2 or, as shown in FIG. 2, can be positioned outside the guide and connected thereto with the aid respectively two output and preferably multimode optical fibers 45 and 47.

If a represents the amplitude of the two reference signals and b the amplitude of the measurement signal, the two detectors 42 and 44 receive a light signal respectively of intensity $I_1$ and $I_2$ equal to:

$$I_1 = a^2 + b^2 + 2ab \cos(P + P_0)$$

$$I_2 = a^2 + b^2 + 2ab \cos(P + P_0 - P_d)$$

with $P_0 = 2\pi n_1 (L_2 - L_1)/\lambda - 2\pi n_1 L/\lambda$
and $P = 2\pi n_2 L/\lambda$.

In these equations, $P_0$ is the constant phase shift introduced between the measurement beam and each reference beam and is independent of the unknown absolute index N of the fluid 31; $n_1$ represents the effective index of the light guide outside the interaction zone 32; $L_2$ and $L_1$ the paths traversed by the light along the measurement beam and the reference beams; L the length of the interaction zone 32; $\lambda$ the wavelength of the guided light; P the unknown phase shift dependent on N (absolute refractive index to be known) via the effective index $n_2$ of the guided light mode in the interaction zone 32; and $P_d$ the constant phase shift introduced by phase shifter 28.

When the phase shift $P + P_0$ is a multiple of $k\pi$ for one of the two systems, it need not be for the other system when two interference systems are used.

Figure 6:
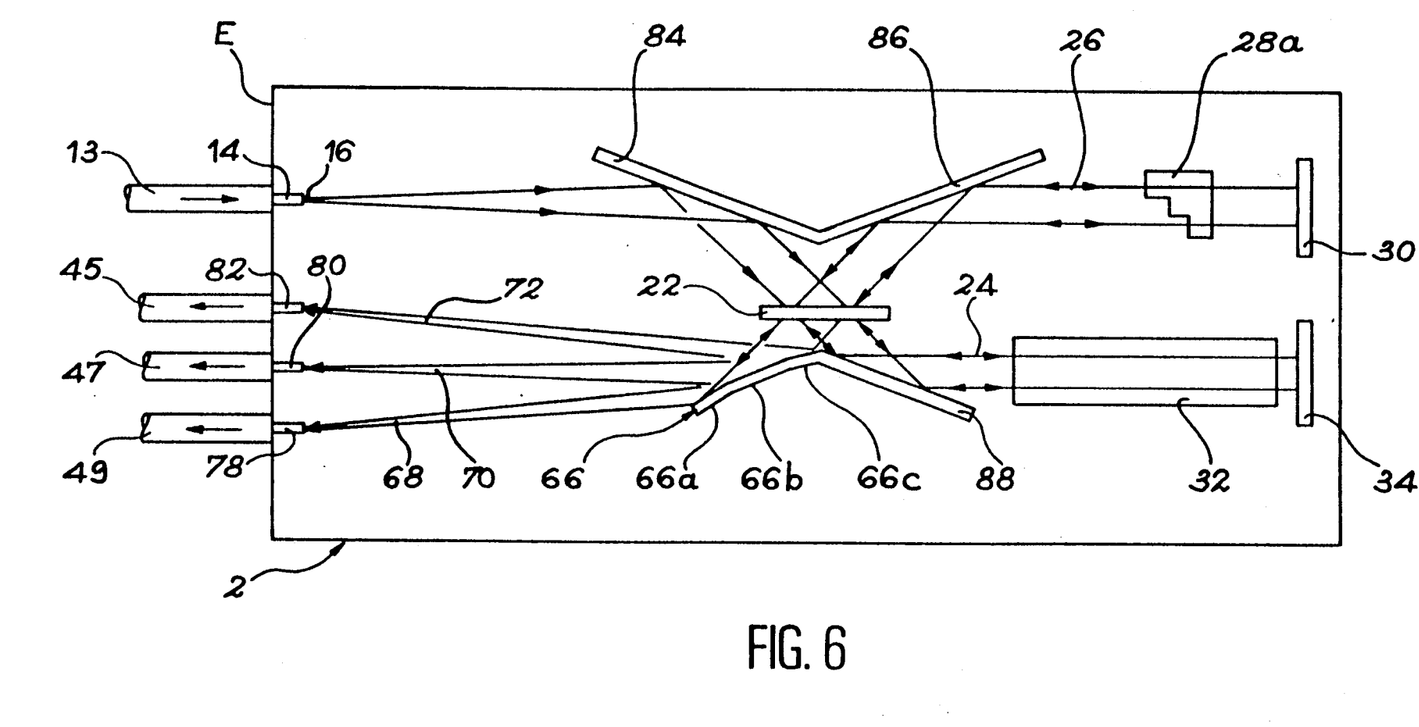
FIG. 6 Diagrammatically and in plan view, a variant of the device according to the invention shown in FIG. 2.

When the index N varies by a value dN (relative index), the effective index of the light guide in the interaction zone 32 varies by $dn_2$ and consequently the phase shift P varies by $dP = 2x\pi dn_2 L/\lambda$, x being the number of passages of the measurement beam in the measurement zone (x=2 in FIGS. 2 and 6).

The length L is chosen as a function of the maximum possible value $dn_2$ ($dn_2$max) in two ways:

a) in such a way that dP is close to $\pi/2$, which gives L close to $\lambda/4 \times dn_2$max. In this case, the intensities $I_1$ and $I_2$ vary between $(a+b)^2$ and $(a-b)^2$, while remaining in the same interference fringe.

b) When L is large compared with $\lambda/2 \times dn_2$max, there is a displacement of the interference fringes, because dP can be well above $2\pi$. It is then necessary to count these interference fringes. If for any reason the measurements can no longer take place (instantaneous stoppage of the device), there can be a loss of previous information, because it is never possible to know by how many entire fringes the interference system has moved during the stoppage period. This is due to the fact that an optical phase shift is only defined to within $2k\pi$ (which leads to multiple solutions for dN and N) and its value is never known in absolute terms and only by comparison with a previous situation. It is preferable to choose a phase shift dP close to $\pi/2$ in order to determine L.

On the basis of the measurement of the intensities $I_1$ and $I_2$ and for case b), while also counting the number of interference fringes of the two systems, $dn_2$ is obtained. On the basis of $dn_2$, it is possible to determine dN either by a prior calibration of the device, or by propagation equations. A prior calibration of the device is the preferred method due to its simplicity and its low error rate. The value of the absolute index can be obtained either directly (solely in the case of a half-fringe, when the extremes of the indexes of the medium 31 are known), or from the relative index dN and the reference index.

With the aid of an appropriate electronic processing device connected to the two photodetectors 42 and 44, it is possible to evaluate an interference fringe fraction. This device makes it possible to determine $dn_2$ and therefore dN and N. Moreover, in case b), said device ensures the counting of the fringes. This electric system 46 is in particular that of the article "Liquid Level Interferometer" by S. S. JACOBS and J. G. SMALL, Applied Optics, vol. 20, No. 20, pp 3508-3513, October 1981.

Figure 3:
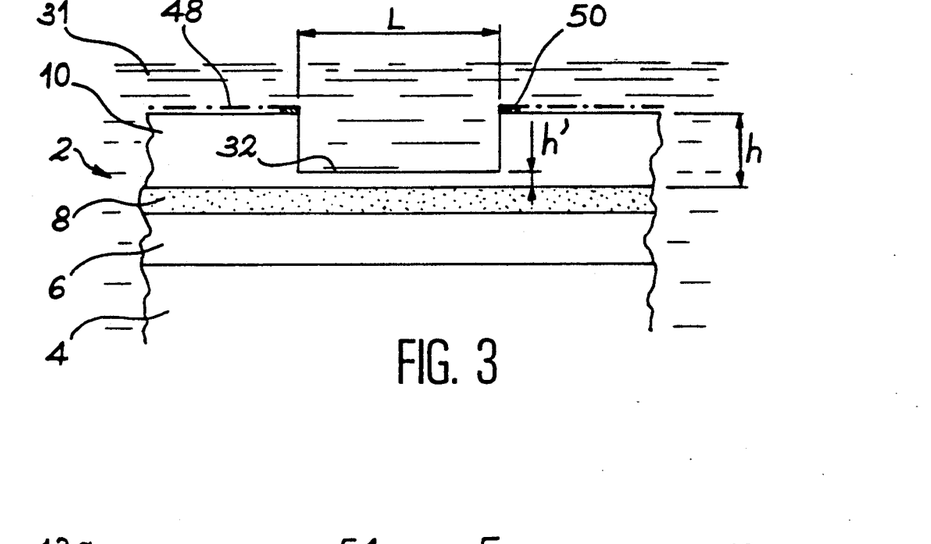
FIG. 3 In section, a first embodiment of the measurement interaction zone of the device of FIG. 2.

FIG. 3 shows an embodiment of the interaction zone 32 with the liquid 31 having an unknown index, in accordance with the invention. In zone 32, thickness h' of the upper silica layer 10 must be smaller than the penetration distance of the evanescent wave associated with the guided mode, whereby h' can be zero. Moreover, the unknown refractive index N must be below the effective index of the guided mode for the light wave to remain guided.

Outside the interaction zone 32, the thickness h of the silica layer 10 must be greater than the penetration distance of the evanescent wave associated with the guided mode. In particular, for a guided wavelength of 800 nm, h must exceed approximately 1 $\mu$m for a $Si_3N_4$, approximately 160 nm thick guided layer 8.

According to the invention, only the interaction zone 32 has to be placed in contact with the unknown fluid 31. Moreover, in order to avoid the deterioration of the sensor, it is possible to protect the latter, outside zone 32, by a protective film 48 e.g. of PTFE or some other material resisting the fluid to be measured in the case of an electrolyte, whereof it is wished to measure the refractive index. Seals 50 are provided all round zone 32 in order to prevent the corrosive medium 31 from coming into contact with the other zones of the optical circuit.

Figure 4:
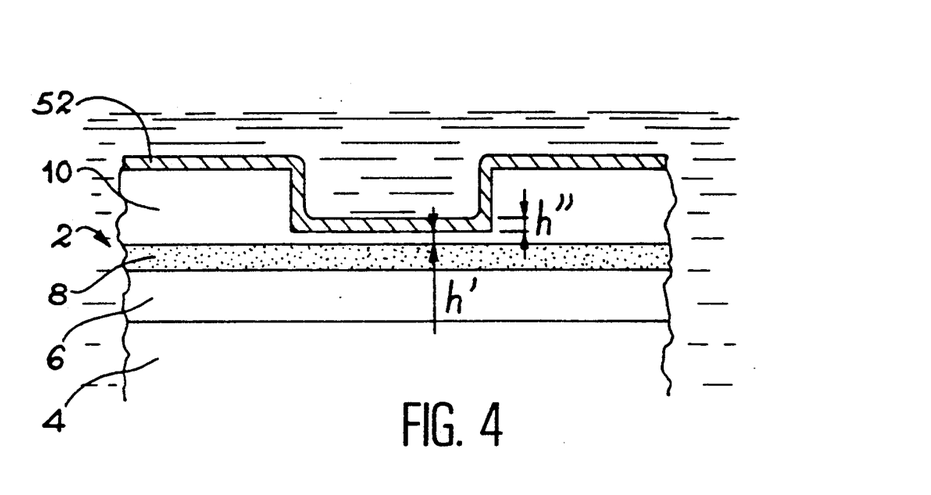
FIG. 4 In section, a second embodiment of the interaction measurement zone of the device of FIG. 2.

As shown in FIG. 4, it is also possible to cover the complete device with a protective layer 52 of thickness h'', so that e.g. h'' + h' is less than the penetration distance of the evanescent wave of the guided mode. Alumina is a good protective material in the case of an acid liquid.

Figure 5:
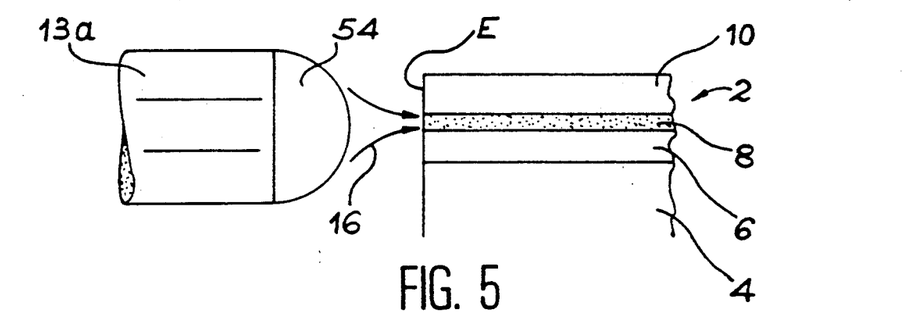
FIG. 5 In section, the coupling of the input optical fiber to the waveguide of the device of FIG. 2.

With a waveguide using a $SiO_2$-doped $Si/SiO_2/SiO_2$ structure, the input fiber 13a, as shown in FIG. 5, can be of a multimode nature. In this case, a collimating lens 54 at the end of the optical fiber 13a must be provided to ensure the injection of light into the layer 8 of the waveguide 2, optionally via a microguide.

The optical device according to the invention shown in FIG. 2 can be modified in the manner shown in FIG. 6. The components of this device, identical to those of FIG. 2, carry the same references.

In this variant, the phase shifter $28_a$ located on the reference beam 26 is a three-channel phase shifter, which in particular makes it possible to obtain freedom from fluctuations in the intensity of the light source 12. The phase shifts $P_d$ used between the three channels are advantageously 0, $(2k+1)\pi/2$ and $(2k+1)\pi$.

For k=0, the use of a three-channel phase shifter makes it possible to obtain three systems of interference fringes of intensity $I_1$, $I_2$ and $I_3$ satisfying the following equations:

$$I_1 = a^2 + b^2 + 2ab \cos(P' - P'_0)$$

$$I_2 = a^2 + b^2 \pm 2ab \sin(P' - P'_0)$$

$$I_3 = a^2 + b^2 - 2ab \cos(P' - P'_0)$$

in which P' is the variable phase shift due to the unknown fluid 31 and $P'_0$ a constant phase shift dependent on the form of the sensor and which is determined by calibrating the latter.

Under these conditions, the variation of the phase shift dP' introduced by the fluid 31 of unknown index satisfies the equation $dP' = d(\text{Arctg}(B))$, in which B is equal to $(2I_2 - I_1 - I_3)/(I_1 - I_3) = \pm \text{tg}(P' - P'_0)$ with $P' - P'_0 = \pm \text{Arctg} B$.

The use of a three-channel phase shifter then requires the use at the output of the optical device of a three-channel splitting mirror 66 having three parts 66a, 66b and 66c having a parabolic shape splitting the three interference signals 68, 70, 72 formed on plate 22. The split or separated interference beams are then transmitted via the output microguides 78, 80, 82 in three multimode output fibers connected to three photodetectors in a similar manner to that of the interference beams (FIG. 2).

It is possible to replace the input collimating lens 18 (FIG. 2) by a parabolic mirror 84, which is a collimating means. Moreover, it is possible to introduce into the measuring device of the invention, plane mirrors 86, 88 in order to form the reference arm 26 and measurement arm 24, which are parallel to one another. The input 13 and output 45, 47, 49 optical fibers are then coupled to the light guide 2 by the same face E and not to two perpendicular faces E and S (FIG. 2). Mirror 84 reflects the incident beam 16 to the splitting plate 22, mirror 86 reflects the reference beam formed on plate 22 to phase shifter 28 and mirror 88 reflects the measurement beam formed on splitting plate 22 to the measurement zone 32. If necessary, the plane mirrors 86 and 88 can be used in a system with two interference signals using as the input collimating optics a lens (FIG. 2).

Figure 7:
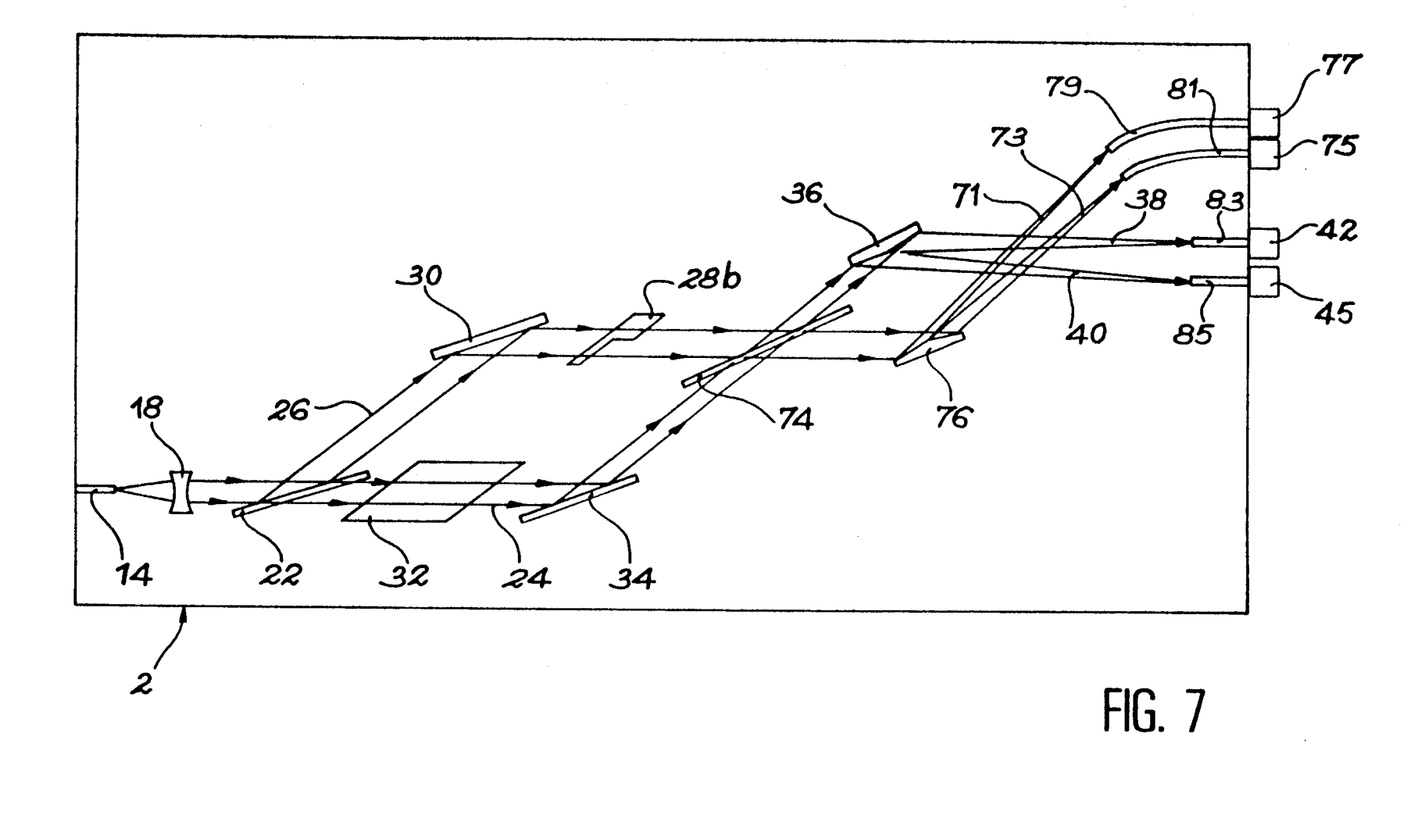
FIG. 7 Diagrammatically and in plan view, a second embodiment of the optical device according to the invention, and FIG. 8 Curves giving the variants $dn_2$ of the effective index of the light guide in the interaction zone, as a function of the absolute refractive index to be determined N.

In the interferometric system shown in FIGS. 2 and 6, the mirrors 30 and 34 are respectively perpendicular to the reference 26 and measurement 24 beams and thus necessarily reflect these beams onto the beam splitting plate 22. According to the invention, the measurement and reference beams 24 and 26 respectively passing out of the plate 22 can respectively act on the mirrors 34 and 30 with an oblique incidence and as shown in FIG. 7. The optical components of the interferometer of FIG. 7 and identical to those of FIG. 2 carry the same references.

In this embodiment, the light beams reflected by mirrors 30 and 34 are then received by another splitting plate 74, formed by a groove etched in light guide 2, on which the interference systems are formed.

In the case of a two-channel phase shifter 28b, there are four such interference systems. The detection of two of these signals, e.g. signals 38 and 40 from the splitting mirror 36 is sufficient for determining the index N of the fluid in contact with the measurement zone 32. However, in certain cases it can be of interest to detect the two other interference systems.

For this purpose, a supplementary splitting mirror 76, positioned downstream of the splitting plate 74, can be provided for giving two separate interference signals 71 and 73, which are respectively detected by two photodetectors 75, 77, which can be attached to guide 2, like detectors 42 and 44, or can be positioned outside the guide 2 and connected to the latter via optical output fibers (FIG. 2). Splitting mirror 76 is identical to splitting mirror 36.

Output microguides 79, 81, 83, 85 can be provided in order to improve the focussing of the interference signals on the detectors 75, 77, 42, 44.

The phase shift 28b responsible for the two secondary reference beams and giving rise to four interference signals, 38, 40, 71 and 73 can be placed between mirror 30 and the beam splitting plate, as shown in FIG. 7, or can be placed upstream of mirror 30, i.e. between the latter and plate 22.

The arrangement of mirrors 30 and 34 of FIG. 7 and the joint use of a second splitting plate 74, a second splitting mirror 76 and two supplementary detectors 75 and 77 can obviously be combined with the embodiment of FIG. 6 using the mirror array 84-86-88.

For a constant phase shift of $\pi/2$ introduced by the two-channel phase shifter 28b, one obtains the four interference systems of intensity $I_1$, $I_2$, $I_3$ and $I_4$ satisfying the following equations:

$$I_1 = a^2 + b^2 + 2ab \cos(P + P_0)$$

$$I_2 = a^2 + b^2 + 2ab \cos(P + P_0 + \pi/2)$$

$$I_3 = a^2 + b^2 - 2ab \cos(P + P_0)$$

$$I_4 = a^2 + b^2 - 2ab \cos(P + P_0 + \pi/2)$$

P and $P_0$ having the same meanings as hereinbefore (FIG. 2).

According to the invention, mirrors 84, 86, 88, 30, 34, 36, 66, 76, lens 18, splitting plates 22, 74, phase shifters 28, 28a or 28b are defined in guide 2 in order to locally modify the value of the effective index of the guided mode.

As shown in FIG. 2, the lens can be produced by anisotropic etching of the complete layer 10, the dimensions and shape respectively defining the dimensions and optical properties of said lens.

It is possible to obtain the beam splitting plates 22 and 74 by partial anisotropic etching of the light guide, or in the form of a network operating under Bragg conditions and the phase shifters 28, 28a, 28b by partly etching the light guide in an anisotropic manner.

Particularly in the case of a $SiO_2/Si_3N_4/SiO_2$ light guide, the splitting plates 22 and 74, together with the phase shifters 28, 28a or 28b are produced by total anisotropic etching of layer 10.

As indicated in FIG. 2, mirrors 30, 34, 36, 66, 76, 84 and 86 can be produced by complete etching of optical guide 2 down to substrate 4, an anisotropic etching of the guide making it possible to obtain perfectly abrupt etched sides. In order to improve their reflection characteristics, it is possible to cover the etched sides with a gold or aluminium film.

For further details regarding the production of the different integrated components of the sensor according to the invention, reference can be made to French patent application 87 04 877 filed in the name of the present applicant.

Figure 8:
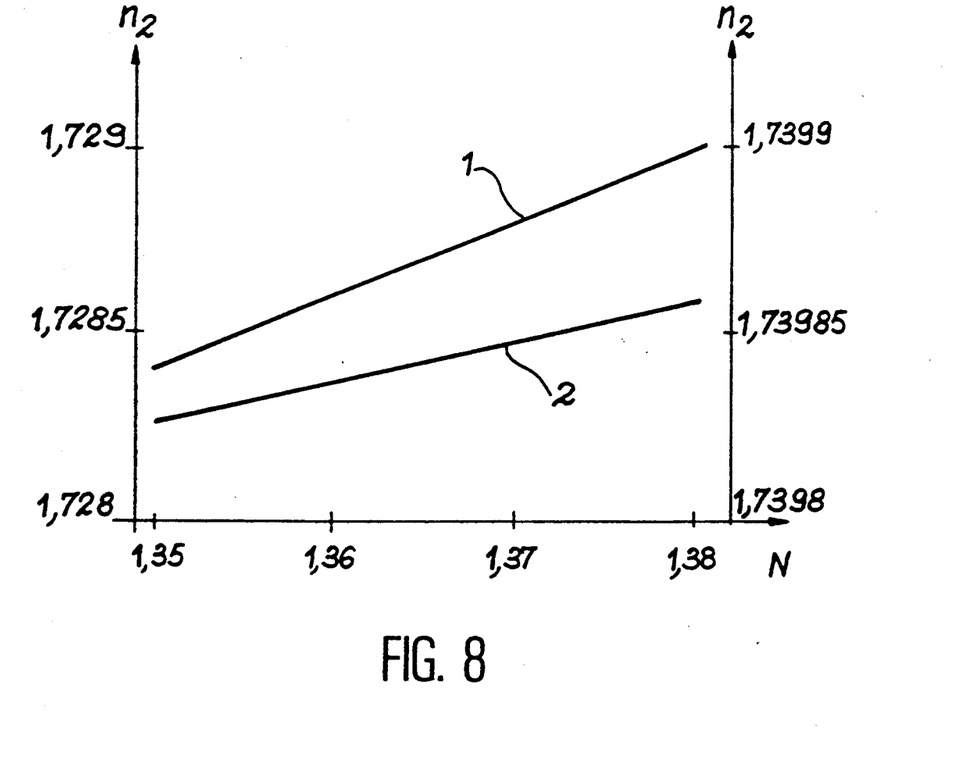

Hereinafter are given two examples for determining the refractive index N of an unknown liquid (e.g. electrolyte), with reference to FIG. 8, which gives the variations of the effective index of the guide in zone 32 as a function of the variations of index N.

Curve 1 corresponds to a sensor formed in a Si/SiO$_2$/Si$_3$N$_4$/Al$_2$O$_3$ structure, the SiO$_2$, Si$_3$N$_4$ and Al$_2$O$_3$ layers having a refractive index of respectively 1.453, 1996 and 1.61 and respective thicknesses of 2 µm, 165 nm and 150 nm.

Curve 2 corresponds to a sensor formed in a structure only differing from the preceding structure by the alumina layer thickness, which is 400 instead of 150 nm.

Thus, the effective index n$_2$ of the interaction zone 32 varies with the index N of the electrolyte (which varies here from 1.35 to 1.38). The values n$_2$ for curves 1 and 2 are respectively read on the ordinate axes to the left and right of the drawing.

The light phase displacement P consequently also varies with the index N of the value dP giving:

$$dP = x \cdot \frac{2\pi}{\lambda} (n_2(N) - n_2(N_0))L$$

with λ being the optical wavelength used; L the interaction length of the structure with the electrolyte; n$_2$(N) the effective index of the guided mode for a value N of the refractive index of the electrolyte; n$_2$(N$_0$) the effective index of the guided mode for a value N$_0$ of the refractive index of the electrolyte (e.g. N$_0$=1.35).

The factor x in this equation corresponds to the number of light passages in the interaction zone 32 (x=1 in FIG. 7 and x=2 in FIGS. 2 and 6).

In general, to ensure a good linearity of the measurement of P, the maximum phase shift designated dP$_{max}$ is chosen, so that:

$$dP_{max} = x \cdot \frac{2\pi}{\lambda} dn_{2max} L \text{ is close to } \frac{\pi}{2}$$

which gives as the value of L:

$$L \approx \lambda/4 \cdot x d n_{2max}.$$

In our example:

$$dn_{2max} = n_2(1.38) - n_2(1.35).$$

Thus, as a function of the structures used for the interaction zone 32 (curve 1 or 2), dn$_{2max}$ can differ widely: dn$_{2max} \approx 5 \cdot 10^{-4}$ for the structure corresponding to curve 1 and dn$_{2max} = 2.5 \cdot 10^{-5}$ for the structure corresponding to curve 2.

Thus, for the structure of curve 1 L≈200 µm is chosen and for that of curve 2 L≈4 µm with λ=0.8 µm and x=2.

This makes it possible to average out to a greater or lesser extent the values of the index N to be measured over a varying interaction length.

We claim:

1. An integrated optical device for measuring the refractive index of a fluid comprising (a) a light guide (2) corresponding to an effective index n$_1$ of the guided mode, formed on a substrate (4) and having a guiding layer (8) for carrying light beams (16, 24, 26, 38, 40), inserted between a lower layer (6) and an upper layer (10) having refractive indices below that of the guiding layer (8), (b) an interaction measuring zone (32) of the light guide to be in contact with the fluid (31), the upper layer level (10) with the measuring zone having a thickness (h') smaller than the penetration distance of the evanescent wave of the guided light beam and outside said interaction zone a thickness (h) greater than the penetration distance of said same evanescent wave, and (c) an interferometric optical system, at least partly formed in the light guide and having a reference optical circuit (22, 28, 28a, 30) and a measuring optical circuit (22, 32, 34) including the measuring zone (32), in order to measure the phase shift introduced by a change to the effective index n$_2$ of the guided mode due to the fluid.

2. The optical device according to claim 1, characterized in that the upper layer (10) of the guide is coated with a protective layer (52), whose thickness (h") at the measurement zone (32) is such that the sum of the thicknesses (h'+h") of the upper layer (10) and the protective layer (52) at the interaction zone (32) is less than the penetration distance of the evanescent wave when the protective layer has a refractive index below the effective index of the guided mode.

3. The optical device according to claim 1, characterized in that a protection system (48) equipped with seals (50) insulates the measurement zone (32) from the measurement and reference optical circuits.

4. The optical device according to claim 1, characterized in that the guiding layer (8) is of silicon nitride or doped silica and the lower (6) and upper (10) layers of pure silica.

5. The optical device according to claim 2, characterized in that the protective layer (52) is of alumina.

6. The optical device according to claim 1, characterized in that the optical components of the interferometric system are all formed by local modification of the light guide.

7. The optical device according to any one of the claims 1 to 6, characterized in that it comprises:
a light source (12) emitting a main incident light beam (16),
means (18, 84) for collimating the main beam,
first splitting means (22) for splitting the collimated main beam into a measured beam (24) and a main reference beam (26) and for directing the measurement beam (24) onto the measurement zone (32),
a first mirror (34) for reflecting the measurement beam (24) from the measurement zone onto the first splitting means (22),
phase shifting means (28, 28a, 28b) for introducing at least one constant phase shift on part of the main reference beam (26), in order to form at least two secondary phase shifted reference beams,
a second mirror (30) for reflecting the two secondary reference beams onto the first splitting means (22), in order to make them respectively interfere with the measurement beam and thus form at least two first separate interference light signals (38; 40; 68, 70, 72), said first interference signals representing the refractive index of the fluid (31) in contact with the measurement zone,
second splitting means (36, 66) for splitting the first two interference signals and
at least two detectors (42, 44) for in each case detecting a first interference signal,
the collimation means (18, 84), the first and second splitting means (22, 36, 66) and the phase shifting means being respectively formed by an appropriate local modification of the effective index of the light beam, and the mirrors (30, 34) being formed by a local and at least partial etching of the light guide.

8. Optical device according to claim 7, characterized in that an optical input fiber (13, 13a), associated with an input microguide (14) formed on substrate (4) is placed between the light source (12) and the collimating means (18, 84), in order to direct the main beam onto the collimating means.

9. The optical device according to claim 7, characterized in that supplementary splitting means (76) associated with second detectors (75, 77) are provided for splitting and detecting second interference signals (71, 73) representative of the refractive index of fluid (31).

10. The optical device according to claim 9, characterized in that at least one of the first (22), second (36, 66) and third (74) splitting means, on the one hand, and the supplementary splitting means (76), on the other hand, are formed by an etched side of the light guide extending up to the substrate (44).

11. The optical device according to claim 7, characterized in that optical output fiber (45, 47, 49), associated with output microguides (78, 80, 82, 79, 81, 83, 85) formed on the substrate are provided upstream of the first and/or second detectors (42, 44, 75, 77), in order to direct the interference signals onto the detectors.

12. The optical device according to claim 7, characterized in that a third reflecting mirror (86) is placed between the first splitting means (22) and the phase shifting means (28a) and in that said mirror is formed by local and at least partial etching of light guide (2).

13. The optical device according to claim 7, characterized in that a fourth reflecting mirror (88) is placed between the first splitting means (22) and the measurement zone (32) and is formed by a local and at least partial etching of the light guide.

14. The optical device according to claim 13, characterized in that the first, second, third and fourth mirrors are formed by an etched side of the light guide extending up to the substrate (4).

15. The optical device according to claim 7, characterized in that the phase shifting means (28a) are constituted by three phase shifters thus forming three secondary reference beams interfering with the measurement beam in order to form three first interference signals (68, 70, 72).

16. The optical device according to claim 1, characterized in that it comprises:

a light source (12) emitting a main incident light beam (16), means (18, 84) for collimating the main beam, first splitting means (22) for splitting the main collimated beam into a measurement beam (24) and a main reference beam (26) and for directing the measurement beam (24) onto the measurement zone (32), a first mirror (34) for reflecting the measurement beam (24) from the measurement zone onto second splitting means (74), phase shifting means (28, 28a, 28b) for introducing at least one constant phase shift onto part of the main reference beam (26), in order to form at least two secondary phase shifted reference beams, a second mirror (30) for reflecting the two secondary reference beams onto the second splitting means (74), so as to respectively make them interfere with the measurement beam and thus form at least two first separate interference light signals (38; 40; 68, 70, 72), said first interference signals representing the refractive index of the fluid (31) in contact with the measurement zone, third splitting means (36, 66) for splitting the first two interference signals and at least two detectors (42, 44) for in each case detecting a first interference signal, the collimating means (18, 84), the first, second and third splitting means (22, 36, 66, 74) and the phase shifting means being respectively formed by an appropriate local modification of the effective index of the light guide, and the mirrors (30, 34) being formed by a local and at least partial etching of the light guide.

17. The optical device according to claim 16, characterized in that an optical input fiber (13, 13a), associated with an input microguide (14) formed on substrate (4) is placed between the light source (12) and the collimating means (18, 84), in order to direct the main beam onto the collimating means.

18. The optical device according to claim 16, characterized in that supplementary splitting means (76) associated with second detectors (75, 77) are provided for splitting and detecting second interference signals (71, 73) representative of the refractive index of said fluid (31).

19. The optical device according to claim 16, characterized in that optical output fibers (45, 47, 49), associated with output microguides (78, 80, 82, 79, 81, 83, 85) formed on the substrate are provided upstream of at least one of said first and second detectors (42, 44, 75, 77), in order to direct the interference signals onto the detectors.

20. The optical device according to claim 16, characterized in that a third reflecting mirror (86) is placed between the first splitting means (22) and the phase shifting means (28a) and in that said mirror is formed by local and at least partial etching of light guide (2).

21. The optical device according to claim 16, characterized in that a fourth reflecting mirror (88) is placed between the first splitting means (22) and the measurement zone (32) and is formed by a local and at least partial etching of the light guide.

22. The optical device according to claim 16, characterized in that the phase shifting means (28a) are constituted by three phase shifters thus forming three secondary reference beams interfering with the measurement beam in order to form three first interference signals (68, 70, 72).

23. The optical device according to claim 1, characterized in that the length L of the measurement zone (32) is equal to approximately $\lambda/4x \cdot dn_2 max$ with $\lambda$ being the wavelength of the guided mode, $dn_2 max$ the maximum possible variations of the effective index of the guided mode in the measurement zone and x the number of passages of the measurement beam (24) in the measurement zone.

* * * * *